(12) United States Patent
Tarter et al.

(10) Patent No.: US 7,914,463 B2
(45) Date of Patent: Mar. 29, 2011

(54) DOUBLE CORE BIOPSY INSTRUMENTATION KIT

(75) Inventors: Thomas Tarter, Springfield, IL (US); Julie Tarter, Springfield, IL (US); Ajay Mahajan, Murphysboro, IL (US); Brad Schwartz, Springfield, IL (US); Chu Tsuchin, Carbondale, IL (US)

(73) Assignee: Clipius Technologies, Inc., Springfield, IL (US)

( * ) Notice: Subject to any disclaimer, the term of this patent is extended or adjusted under 35 U.S.C. 154(b) by 19 days.

(21) Appl. No.: 11/551,784

(22) Filed: Oct. 23, 2006

(65) Prior Publication Data

US 2008/0114265 A1    May 15, 2008

(51) Int. Cl.
*A61B 10/00* (2006.01)
(52) U.S. Cl. .................................................. 600/567
(58) Field of Classification Search ............... 600/567, 600/564, 565, 569, 566, 570, 568
See application file for complete search history.

(56) References Cited

U.S. PATENT DOCUMENTS

| | | |
|---|---|---|
| 3,106,483 A | 10/1963 | Kline et al. |
| 3,358,648 A | 12/1967 | Berens |
| 4,708,147 A | 11/1987 | Haaga |
| 4,903,709 A | 2/1990 | Skinner |
| 4,958,625 A | 9/1990 | Bates et al. |
| 5,106,364 A | 4/1992 | Hayafuji et al. |
| 5,121,751 A | 6/1992 | Panalletta |
| 5,195,533 A | 3/1993 | Chin et al. |
| 5,224,488 A | 7/1993 | Neuffer |
| 5,243,994 A | 9/1993 | Ranalletta |
| 5,251,641 A | 10/1993 | Xavier |
| 5,368,045 A | 11/1994 | Clement et al. |
| 5,394,887 A | 3/1995 | Haaga |
| 5,449,001 A | 9/1995 | Terwilliger |
| 5,462,062 A | 10/1995 | Rubinstein et al. |
| 5,469,860 A | 11/1995 | De Santis |
| 5,511,556 A | 4/1996 | DeSantis |
| 5,526,821 A | 6/1996 | Jamshidi |
| 5,526,822 A | 6/1996 | Burbank et al. |
| 5,535,755 A | 7/1996 | Heske |
| 5,560,373 A | 10/1996 | De Santis |
| 5,595,185 A | 1/1997 | Erlich |
| 5,649,547 A | 7/1997 | Ritchart et al. |
| 5,752,069 A | 5/1998 | Roberts et al. |
| 5,775,333 A | 7/1998 | Burbank et al. |
| 5,817,033 A | 10/1998 | DeSantis et al. |
| 5,823,970 A | 10/1998 | Terwilliger |
| 5,916,229 A | 6/1999 | Evans |
| 5,922,003 A | 7/1999 | Anctil et al. |

(Continued)

FOREIGN PATENT DOCUMENTS

WO     95/28131     10/1995

*Primary Examiner* — Max Hindenburg
*Assistant Examiner* — Michael C Stout
(74) *Attorney, Agent, or Firm* — Meyertons, Hood, Kivlin, Kowert & Goetzel, P.C.; Eric B. Meyertons

(57) ABSTRACT

A biopsy needle for collecting tissue samples includes a needle having a first cavity adapted for accepting a first sample core, the needle having a second cavity adapted for accepting a second sample core and a sheath with a single slot or opening and positioned coaxially with the needle. The needle with the sheath may have a separate core extraction kit.

15 Claims, 5 Drawing Sheets

U.S. PATENT DOCUMENTS

| | | | |
|---|---|---|---|
| 5,928,164 A | 7/1999 | Burbank et al. | |
| 5,944,673 A | 8/1999 | Gregoire et al. | |
| 5,961,534 A | 10/1999 | Banik et al. | |
| 5,964,716 A | 10/1999 | Gregoire et al. | |
| 5,980,469 A | 11/1999 | Burbank et al. | |
| 5,989,196 A | 11/1999 | Chu et al. | |
| 6,015,391 A | 1/2000 | Rishton et al. | |
| 6,077,230 A | 6/2000 | Gregoire et al. | |
| 6,110,129 A | 8/2000 | Terwilliger | |
| 6,328,701 B1 | 12/2001 | Terwilliger | |
| 6,428,486 B2 | 8/2002 | Ritchart et al. | |
| 6,709,408 B2 | 3/2004 | Fisher | |
| 6,730,045 B2 | 5/2004 | Finer | |
| 6,860,868 B1 | 3/2005 | Sussman et al. | |
| 6,872,185 B2 | 3/2005 | Fisher | |
| 6,875,183 B2 | 4/2005 | Cervi | |
| 6,908,440 B2 | 6/2005 | Fisher | |
| RE38,776 E | 8/2005 | Bauer | |
| 7,018,343 B2 | 3/2006 | Plishka | |
| 7,033,324 B2 | 4/2006 | Giusti et al. | |
| 7,063,672 B2 | 6/2006 | Schramm | |
| 7,147,607 B2 | 12/2006 | Wang | |
| 7,169,114 B2 | 1/2007 | Krause | |
| 7,204,812 B2 | 4/2007 | Wang | |
| 7,226,424 B2 | 6/2007 | Ritchart et al. | |
| 2003/0229293 A1* | 12/2003 | Hibner et al. | 600/567 |
| 2005/0101879 A1* | 5/2005 | Shidham et al. | 600/566 |
| 2006/0089563 A1* | 4/2006 | McAlister et al. | 600/564 |
| 2007/0016099 A1* | 1/2007 | Chin et al. | 600/565 |
| 2007/0213634 A1* | 9/2007 | Teague | 600/564 |

* cited by examiner

DOUBLE CORE BIOPSY INSTRUMENTATION KIT

FIELD OF THE INVENTION

The present invention relates generally to the field of medical devices and more particularly the present invention relates to the method and apparatus for collecting multiple biopsy samples taken from tissue such as but not limited to the prostate, breast, lung, and other parts of the human body for purposes of pathology, genomics/proteomics or other scientific evaluation.

BACKGROUND OF THE INVENTION

Biopsies are usually performed using a biopsy gun which uses a spring-loaded biopsy needle to be inserted into a gland. A sheath is inserted into the tissue sample/core. The needle is then withdrawn, and the sample is removed to be sent to a pathologist for diagnostics. However, if the patient needs a new diagnostics such as for cancer, then additional tissue is needed for genomic or proteomic analysis. Now, the patient is required to undergo a second biopsy procedure. It is desirable under some conditions to obtain the additional tissue from the location of the original tissue. It may be difficult to reinsert the biopsy gun at the same location that was previously used. The results are inaccurate and subjects the patient to an unnecessary procedure.

INCORPORATION BY REFERENCE

U.S. Pat. No. 4,708,147 dated Nov. 24, 1987; U.S. Pat. No. 3,358,648 dated Dec. 19, 1967 and U.S. Pat. No. 3,106,483 dated Oct. 8, 1963 are incorporated by reference herein.

Generally speaking, biopsy needles fall into one of two types, an end cutting needle, commonly referred to as a "Menghini" needle, or, a side cut needle such as the type commercially known as "Tru-cut" needles. Fundamentally, an end cutting needle includes a hollow cutting sheath having an especially configured, circumferentially sharpened, open end at the distal portion thereof. A needle is conventionally inserted into the hollow shaft of the sheath in its "at rest" or un-actuated position and generally extends flush with the open cutting edge of the sheath to close the open end. With the needle thus inserted, the end cutting needle is inserted into the patient until the needle reaches the site of the lesion where the biopsy specimen is to be taken. The sheath is withdrawn and the needle further inserted into the lesion with the result that tissue is cut and fills the now open cutting end of the needle as it travels a slight distance through the lesion to collect the specimen. A suction device can be applied to the proximal portion of the needle to withdraw the tissue sample thus taken. Alternatively, the needle can be rotated to sever the tissue, and the needle is withdrawn from the site. In a typical side cut needle, there is a "solid" inner needle within an outer sheath and the inner needle has a shaped pointed end with a cutting groove formed in the distal portion of the inner needle behind the pointed end. The side cut needle is inserted into the patient until the needle reaches the site of the lesion where the biopsy sample is to be taken. The inner needle is then advanced into the lesion to the point where the specimen is to be taken and rotated so that the cutting groove severs the tissue. The outer sheath advances over the inner needle thus containing or entrapping the specimen within the groove of the inner needle and the outer sheath, and the needle is then withdrawn from the site. There are many biopsy needle designs commercially available or described in the literature. For example, it is known to provide an inner needle within the cutting sheath of the end cutting needle which uses movable jaws extending beyond the distal end of the cutting sheath to sever and extract the biopsy specimen. "Hybrid" sheath and needles are also known. Fundamentally, if the biopsy specimen is removed through the cutting end of the needle it is known and will be referred to hereinafter as a "end-cutting" needle and if the sample is taken from the side of the needle, the needle will be referred to hereinafter as a "side-cutting" needle. The invention described herein is applicable to all end-cutting and side-cutting biopsy needles.

Because most biopsy needles reliably function to remove biopsy specimens, the major concern today with biopsy needles and the procedures governing the use thereof centers about obtaining a second specimen from the same location as a first specimen has been taken. To accurately guide the biopsy needle, percutaneous procedures have been developed to permit visual radiological observation of the instrument inside the body. In conjunction with CT guided biopsies, biopsy needles have been especially designed to provide good CT scanning images. An example of such a needle is disclosed in U.S. Pat. No. 4,708,147 dated Nov. 24, 1987 incorporated herein by reference.

SUMMARY OF THE INVENTION

This invention relates generally to surgical needles and more particularly to a biopsy needle construction and a method for performing a biopsy using the needle construction which simultaneously obtains two biological samples of tissues from substantially the same location. The invention is particularly applicable for removing tissue and like specimens from the human body and will be described with particular reference thereto. However, it will be appreciated by those skilled in the art that the invention has broader applications and may be used for selective extraction of tissue samples and the like from other living matter, such as animals or nonliving matter such as cadavers or phantoms, and conceptually is applicable in a broad sense to any surgical procedure requiring insertion of instruments and the like into any organ where the tissue may be punctured.

Accordingly, it is an object of the invention to provide a needle for biopsy sampling purposes which obtains at least two biopsy samples from approximately the same location by using only one biopsy needle and without the need to reinsert the biopsy needle.

This object is achieved in a biopsy needle which may best be explained by the relative position of its parts before, during and after the biopsy is taken. Fundamentally, the needle has an un-actuated position defined by the position of its parts prior to insertion of the needle in the patient, an actuated position defined by its parts position when the sample is being taken and a retracted position defined again by the position of its parts when the needle is removed from the biopsy site. Generally speaking, the needle of the present invention has an inner cutting needle (which may or may not be hollow depending upon the type of needle) having a distal portion for insertion into the biopsy site and a contiguous proximal portion extending from the distal portion. The distal portion in turn is defined as that length of the inner needle which is inserted into the patient in the actuated position of the needle and the distal portion carries the means for taking the biopsy sample, i.e. side or end cutting. At least one outer hollow sheath being coaxial with and receiving the inner needle is provided. The outer sheath has a proximal portion and a separable distal portion. Positioning devices associated with the proximal portions of either the inner needle or outer sheath or both are manipulated by the physician as the needle is inserted into the site, the biopsy taken and the needle retracted so that the distal portion of the outer sheath is separated from the proximal portion and remains at the biopsy site when the needle is in its retracted position. In accordance with a broader feature of the invention, a method for performing a biopsy using a sheath is disclosed. The method broadly comprises manipulating the biopsy needle to achieve the afore-described positions of the needle to insure accurate placement of the sheath within the biopsy site to obtain at least two samples.

It is thus an object of the invention to provide a sheath for use with any biopsy needle.

It is another object of the invention to provide a method for taking a biopsy specimen which deposits a sheath at the biopsy site.

Still another object of the invention is to provide a modified biopsy needle which permits placement of a sheath within the biopsy site in a relatively easy manner and without undue resistance.

Still another feature of the invention is to provide a biopsy needle which can be readily mass produced without undue expense.

Still yet another object of the invention is to provide a needle which can be readily applied to any conventional biopsy sheath.

Further objects and advantages of the invention will become apparent to those skilled in the art from reading and understanding the following detailed description of species thereof and from the accompanying drawings which illustrate preferred embodiments that the invention may take in physical form and in certain parts and arrangement of parts.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 7:
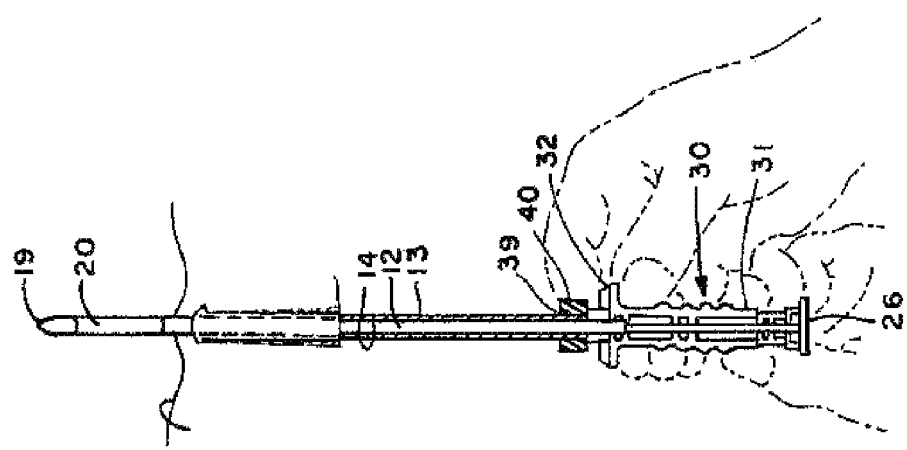
FIG. 7 illustrates a cross-sectional view of a biopsy needle.
Figure 8:
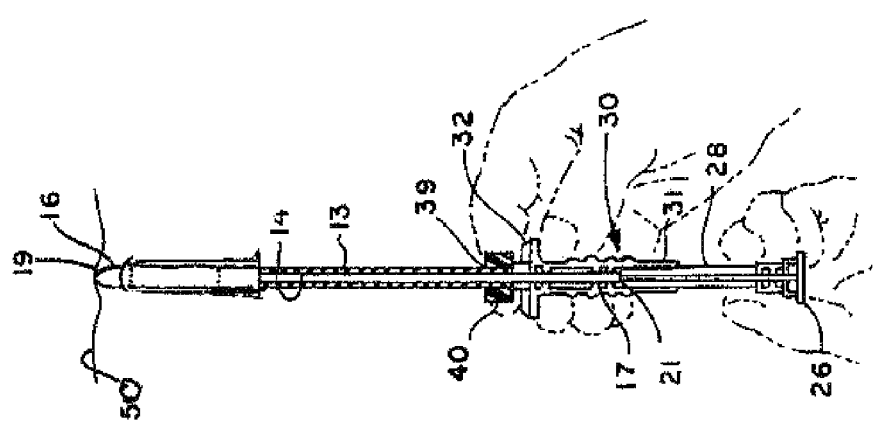
FIG. 8 illustrates a cross-sectional view of the biopsy needle.

Referring now to the drawings wherein the showings are for the purpose of illustrating preferred embodiments of the invention only and not for the purpose of limiting the same, there is shown in FIGS. 7 and 8 a biopsy needle 10 generally defined as comprising an inner or cutting needle 12 which is coaxially received within an outer sheath 13. Cutting needle 12 has a distal portion 16 and contiguous therewith a main or proximal portion 17. Distal portion 16 has an entry end 19 so that needle 10 can enter or puncture the site of the biopsy and a cutting edge 20 which functions to sever the tissue in the lesion for collecting a biopsy sample.

For definitional purposes, distal portion 16 is defined as that body portion of cutting needle 12 which extends from entry end 19 to the end of cutting edge 20, and proximal portion 17 is contiguous with and extends therefrom. The term "cutting needle" is meant to apply to all biopsy needles or medical instruments to which an outer sheath can be fitted for purposes of working the invention as described hereafter. Thus, cutting needle 12 is meant to include various accessories normally used with the sheath. Also meant to be included within the term "cutting needle" are end cutting biopsy needles which have movable jaws at the entry end or hybrid biopsy needles such as the type disclosed in the prior patent referred to above.

Referring now to FIGS. 7 and 8, proximal portion 17 of cutting needle 12 is attached to a positioning mechanism which is shown in a form for ease in explanation. It is contemplated that spring actuated positioning mechanisms now developed for conventional biopsy needles can be modified by those skilled in the art to provide the desired needle positioning as illustrated in the drawings which is achieved by hand manipulation. The bottom end 21 of proximal portion 17 of cutting needle 12 is fixed or rigidly connected to an obturator having an obturator handle 26 and an "X"-shaped plunger portion 28 which is telescopically received within a stem 30 having a base portion 31 ending in a configured easily grip-able handle 32. Plunger portion 28 has a length at least equal to the length of the distal portion 16 of cutting needle 12. As shown in FIGS. 7 and 8, by grasping handle 32 and obturator handle 26, the surgeon can move cutting edge 20 to a forward or retracted position relative to outer sheath 13. Not shown, but contemplated as being attached to cutting needle 12 either at proximal portion 17 or to obturator 25 for actuation at some position thereof, may be a vacuum conduit for applying suction to the interior of cutting needle 12 for purposes of removing the biopsy specimen taken or assuring positioning of the biopsy specimen within cutting needle 12.

Cutting needle 12 is telescopically and co-axially received within an outer sheath 13. Outer sheath 13 has two separate or separable portions defined as a proximal portion 35 and a distal portion 36. Proximal portion 35 in turn has a distal end 38 adjacent distal portion 36 and a proximal end 39 at the opposite end thereof which is fixedly secured as by glue to a pusher handle 40 of the positioning means. As can be seen from FIGS. 7 and 8, pusher handle 40 can telescopically move outer sheath 13 relative to cutting needle 12.

Figure 1:
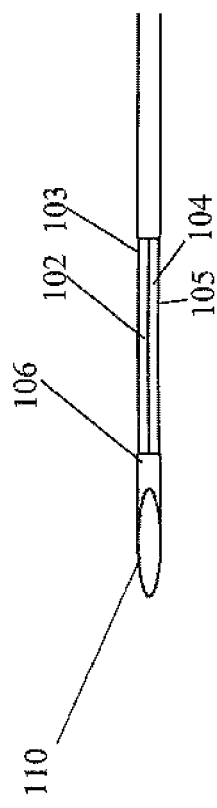
FIG. 1 illustrates a cross-sectional view of the needle of the present invention.

FIG. 1 illustrates a needle 100 of the present invention. The needle 100 includes a first cavity 102 to hold a first core 103 which is a tissue sample taken from a location and a second cavity 104 to hold a second core 105 which is another tissue sample taken from substantially the same location. The first cavity 102 is formed in the housing 106 of the needle 100. The housing 106 is hollow in this embodiment and the first cavity 102 and the second cavity 104 are in communication with the opening 110 at the distal end of the needle 100. The tissue enters the opening 110 and is separated to form the first core 103 and the second core 105. The first core 103 is positioned in the first cavity 102 for subsequent removal, and the second core 105 is positioned in the second cavity 104 for subsequent removal. For example, one core could be used for pathological diagnoses and, for example, if cancer is detected, the second core can be used for molecular analysis. The second cavity 104 is formed in the housing 106.

The first cavity 102 and the second cavity 104 are shown as being formed in the longitudinal direction of the needle 100 and are shown as being substantial rectangles having a length which generally exceeds the width. Other shapes and dimensions are within the scope of the invention.

Figure 2:
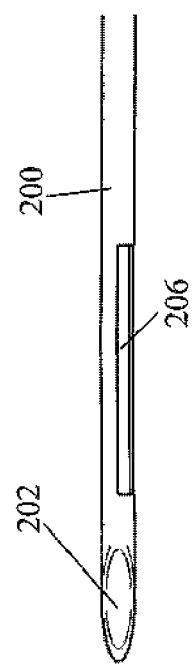
FIG. 2 illustrates a cross-sectional view of the sheath of the present invention.
Figure 9:
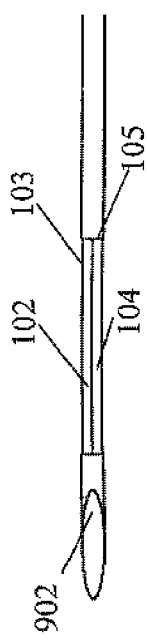
FIG. 9 illustrates a cross-sectional view of the needle of the present invention.

FIG. 2 illustrates a sheath 200 having an opening 202 at a distal end of the hollow housing 204 of the sheath 200. The opening 202 of the hollow housing 204 coaxially receives the needle 100 so that the sheath 200 can rotate with respect to the needle 100. The housing 204 includes a slot 206 to allow access to the first cavity 102 or alternatively to the second cavity 104. The hollow housing 204 rotates so that the slot 206 is positioned in a first position over the first cavity 102. While in this first position, the first core 103 can be removed from the first cavity 102. The hollow housing 204 can be rotated to position in a second position the slot 206 over the second cavity 104. While in this second position, the second core 105 can be removed from the second cavity 104.

Figure 3:
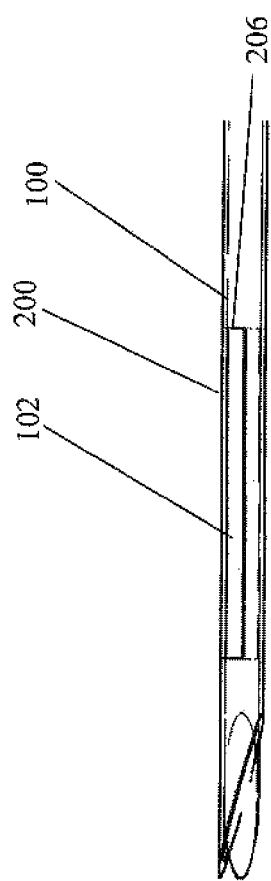
FIG. 3 illustrates a cross-sectional view of the needle and sheath of the present invention.

FIG. 3 illustrates the needle 100 coaxially positioned within the sheath 200. The slot 206 of a sheath 200 is positioned over the first cavity 102 of the needle 100 in the first position so that the first core can be removed.

Figure 4:
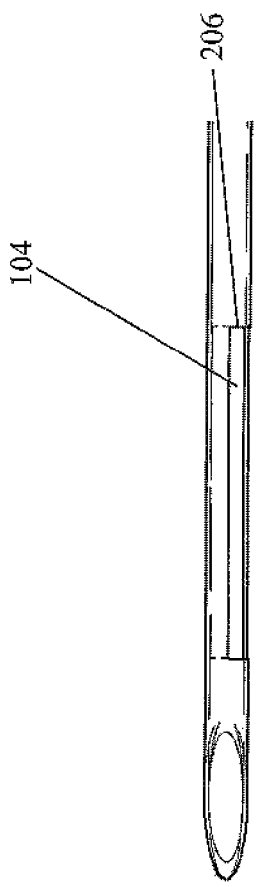
FIG. 4 illustrates another cross-sectional view of the needle and sheath of the present invention.

FIG. 4 illustrates the needle 100 positioned within the sheath 200, but the sheath 200 has been rotated with respect to the needle 100 so that the slot 206 is now positioned over the second cavity 104 of the needle 100 at the second position so that the second core can be removed.

Figure 5:
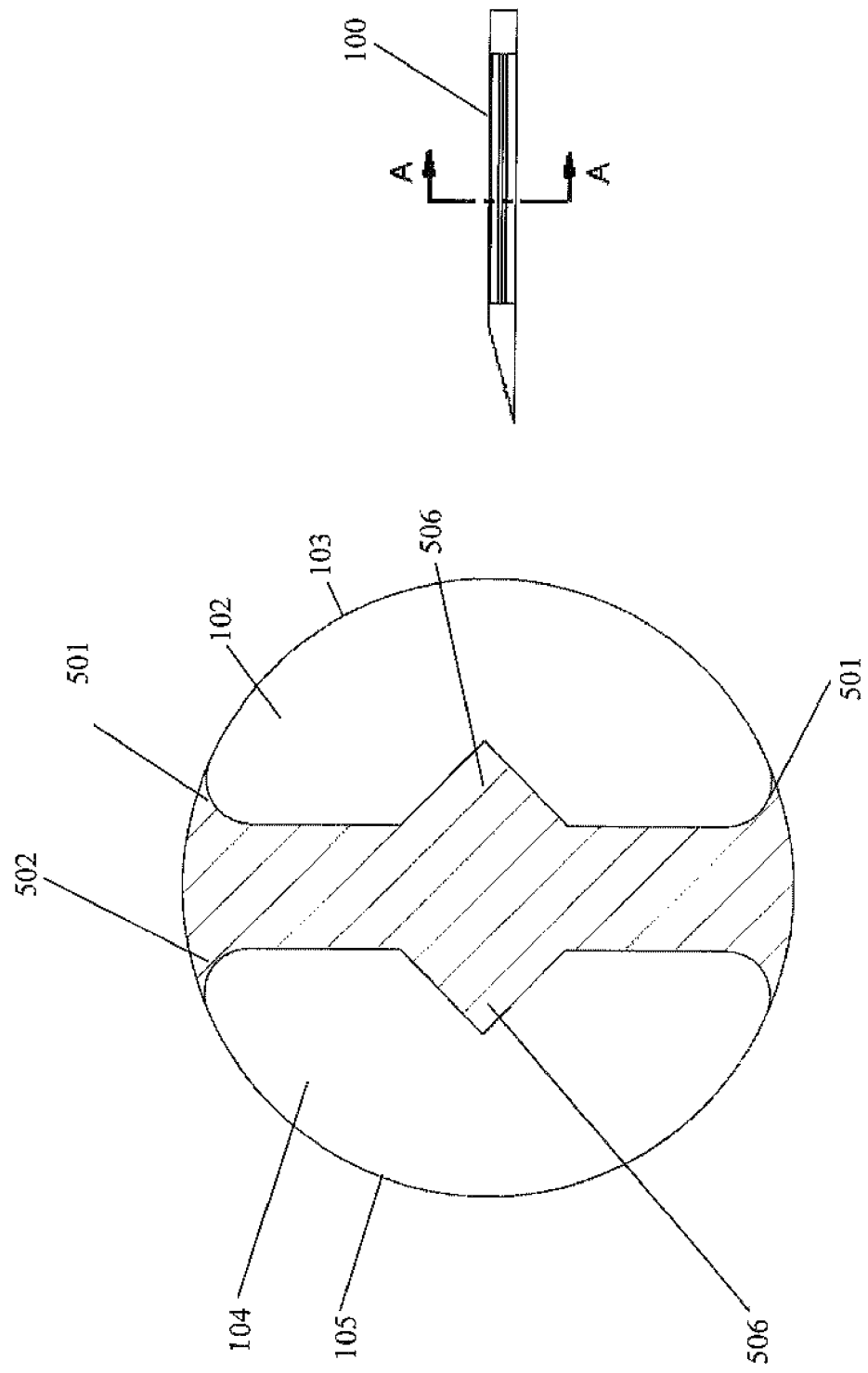
FIG. 5 illustrates a cross-sectional view of the needle of the present invention.

FIG. 5 illustrates a cross-sectional view of the needle 100 showing the first cavity 102 and the second cavity 104. The first cavity 102 and the second cavity 104 share a common wall 502. The common wall 502 includes a concave portion 501 at a distal and proximate end of the common wall 502, and the first cavity 102 and the second cavity 104 extend from the concave portion 501 at one end of the common wall 502 to another concave portion 501 at the other end of the common wall 502.

Additionally, the common wall 502 includes an outwardly extending portion 506 which extends outwards from the common wall 502 in order to aid in the removal of the first or second core. The outwardly extending portion 506 is shown approximately in the center of the common wall 502.

Figure 6:
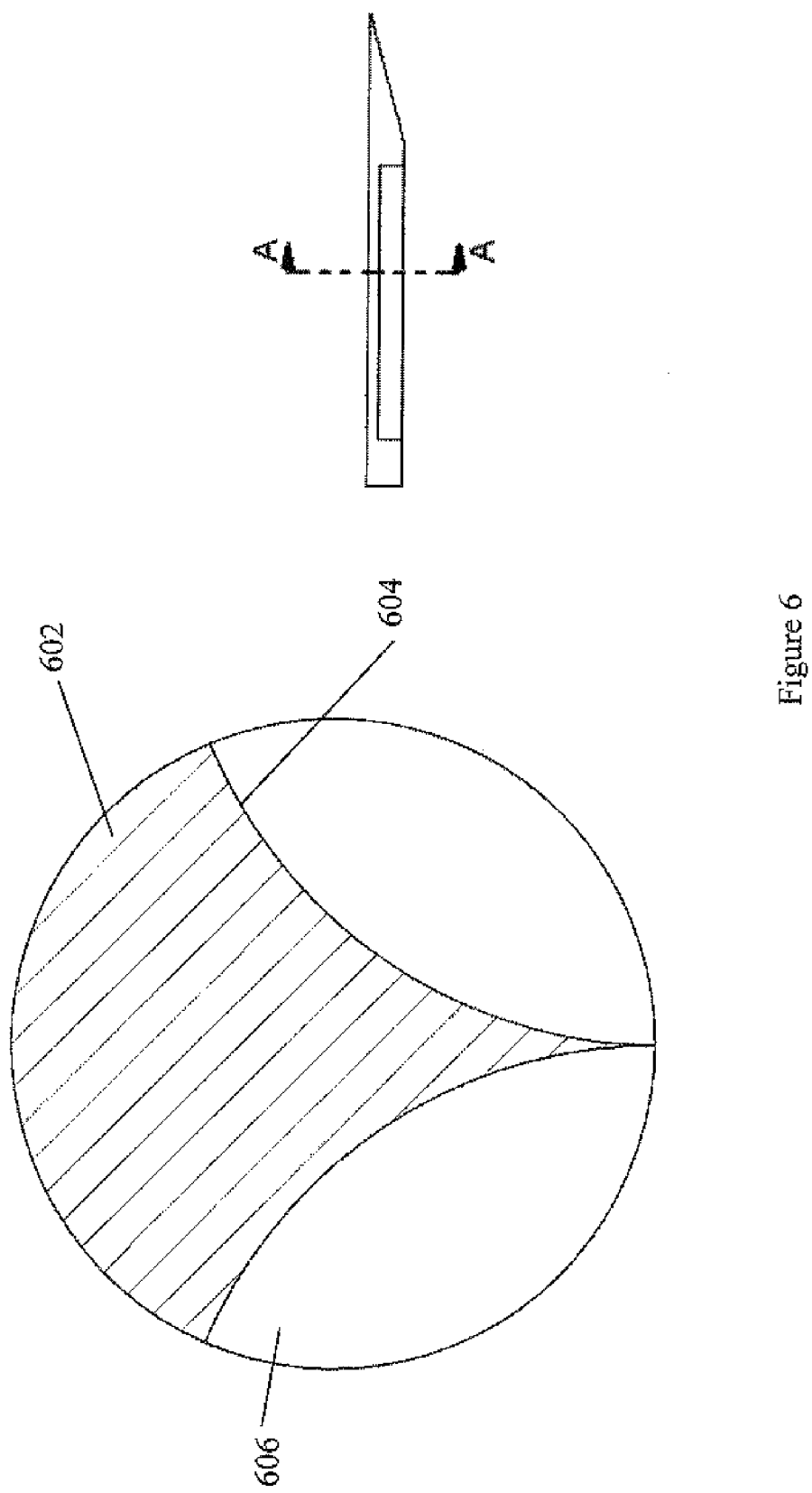
FIG. 6 illustrates a cross-sectional view of the needle of the present invention.

FIG. 6 illustrates a second cross-cross-sectional view of the first cavity 102 and the second cavity 104. The second common wall 602 includes a first concave surface 604 to define the first cavity 102 and a second concave surface 606 to define the second cavity 104. The second common wall 602 has an increasing thickness.

The above described biopsy needle is used to collect two biopsy cores from substantially the same location. The proposed design is a biopsy needle and sample kit. The biopsy needle could come in multiple embodiments by which the sheath is closed on at least two tissue samples simultaneously. While the present invention has been described in terms of obtaining two tissue samples, the teachings of the present invention can be extended to obtaining three or more samples simultaneously. Each core obtained can be used by a different user. For example, one core could be used for a pathologist for a pathologic diagnoses and the other core could be used for molecular grading using genomic or other genetic/scientific analysis. Two cross sections have been shown and other cross sections are within the scope of the invention. The cores obtained by the present invention are shown having the same approximate length and size.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

The invention claimed is:

1. A biopsy needle for extracting multiple cores from the same area, comprising:
    a having a first cavity configured to accept a first sample core,
    a second cavity configured to accept a second sample core, and an opening configured to receive the first sample core and the second sample core; and
    a sheath positioned coaxially with said needle wherein said sheath has a substantially open end portion and wherein the sheath is configured to pass a tissue sample forming the first sample core and the second sample core through the open end portion of the sheath, through the opening of the needle and into the respective first cavity and second cavity;
    wherein the sheath and the needle are positioned coaxially along a longitudinal axis, and wherein the sheath is configured to pass tissue longitudinally into the first cavity and the second cavity such that a wall separating the first cavity and the second cavity is configured to separate the tissue sample into the first sample core that is advanced longitudinally into the first cavity and the second sample core that is advanced longitudinally into the second cavity.

2. The biopsy needle of claim 1, wherein said sheath includes a hollow housing with a slot to access said first cavity and said second cavity.

3. The biopsy needle of claim 1, wherein said wall includes a first concave portion at a distal end of said first cavity.

4. The biopsy needle of claim 1, wherein said wall includes a second concave portion at a proximal end of said first cavity.

5. The biopsy needle of claim 1, wherein said wall increases in thickness (best shown in FIG. 13a).

6. A method for forming a biopsy needle for extracting multiple cores from the same area, comprising:
    positioning a wall in a needle, the wall separating the interior of the needle into at least a first cavity configured to accept a first sample core, and
    a second cavity configured to accept a second sample core;
    wherein an opening in the needle is configured to receive the first sample core and the second sample core; and
    forming a sheath positioned coaxially with said needle, wherein said sheath has a substantially open end portion and wherein the sheath is configured to pass a tissue sample forming the first sample core and the second sample core through the open end portion of the sheath through the opening of the needle and into the respective first cavity and second cavity;
    wherein the sheath and the needle are positioned coaxially along a longitudinal axis, and wherein the sheath is configured to pass tissue longitudinally into the first cavity and the second cavity such that the wall separating the first cavity and the second cavity is configured to separate the tissue sample into the first sample core that is advanced longitudinally into the first cavity and the second sample core that is advanced longitudinally into the second cavity.

7. The method of claim 6, wherein forming said sheath includes forming a hollow housing with a slot to access said first cavity and said second cavity.

8. The method of claim 6, wherein said wall includes a first concave portion at a distal end of said first cavity.

9. The method of claim 6, wherein said wall includes a second concave portion at a proximal end of said first cavity.

10. The method of claim 6, wherein said wall increases in thickness.

11. An apparatus for performing a biopsy, comprising: a needle comprising a first cavity for receiving a first sample core, a second cavity for receiving a second sample core, and an opening configured to receive the first sample core and the second sample core, wherein the first sample core and the second sample core are comprised of tissue; and a sheath positioned coaxially with said needle, wherein said sheath has a substantially open end portion and wherein the sheath is configured to pass a tissue sample forming the first sample core and the second sample core through the open end portion of the sheath, through the opening of the needle and into the respective first cavity and second cavity, a sheath positioned coaxially with said needle, wherein the sheath comprises at least one side slot configured to allow side access to one of said first cavity or said second cavity; wherein the sheath and the needle are positioned coaxially along a longitudinal axis, and wherein the sheath is configured to pass tissue longitudinally into the first cavity and the second cavity such that a wall separating the first cavity and the second cavity is configured to separate the tissue sample into the first sample core that is advanced longitudinally into the first cavity and the second sample core that is advanced longitudinally into the second cavity, and wherein the sheath is operable to be placed in a first position or a second position relative to the needle to provide alternate side access to one of the first cavity or the second cavity through the at least one side slot.

12. The apparatus of claim 11, wherein the sheath is operable to be placed in a third position in which neither the first cavity nor the second cavity is accessible through the at least one side slot.

13. The biopsy needle of claim 1, wherein the sheath comprises at least one side slot configured to allow side access to one of said first cavity or said second cavity, wherein the sheath is operable to be placed in a first position or a second position relative to the needle to provide alternate side access to one of the first cavity or the second cavity through the at least one side slot.

14. The apparatus of claim 13, wherein the sheath is operable to be placed in a third position in which neither the first cavity nor the second cavity is accessible through the at least one side slot.

15. The method of claim 6, further comprising forming at least one side slot in the sheath configured to allow side access to one of said first cavity or said second cavity, wherein the sheath is operable to be placed in a first position or a second position relative to the needle to provide alternate side access to one of the first cavity or the second cavity through the at least one side slot.

\* \* \* \* \*

UNITED STATES PATENT AND TRADEMARK OFFICE
CERTIFICATE OF CORRECTION

PATENT NO. : 7,914,463 B2  Page 1 of 1
APPLICATION NO. : 11/551784
DATED : March 29, 2011
INVENTOR(S) : Tarter et al.

It is certified that error appears in the above-identified patent and that said Letters Patent is hereby corrected as shown below:

Claim 1, col. 6, line 4, please delete "a having" and substitute therefor -- a needle having --.

Signed and Sealed this
Twenty-eighth Day of August, 2012

David J. Kappos
*Director of the United States Patent and Trademark Office*